United States Patent
Ortner et al.

(10) Patent No.: US 8,802,012 B2
(45) Date of Patent: Aug. 12, 2014

(54) METHOD AND DEVICE FOR PRODUCING A FRAGRANCED AIR STREAM

(75) Inventors: Georg Ortner, Köln (DE); Olof Källgren, Pullach (DE)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 13/465,004

(22) Filed: May 6, 2012

(65) Prior Publication Data

US 2012/0280053 A1    Nov. 8, 2012

Related U.S. Application Data

(63) Continuation of application No. PCT/EP2010/006748, filed on Nov. 5, 2010.

(51) Int. Cl.
*A61L 9/14*    (2006.01)

(52) U.S. Cl.
USPC ............... 422/120; 422/5; 422/123; 239/1

(58) Field of Classification Search
USPC ............... 239/1, 304; 422/5, 120, 123
See application file for complete search history.

(56) References Cited

U.S. PATENT DOCUMENTS

| | | | | |
|---|---|---|---|---|
| 3,820,457 A | * | 6/1974 | Bullock | 101/244 |
| 6,136,277 A | | 10/2000 | Nardini | |
| 2004/0003812 A1 | | 1/2004 | Manne | |

FOREIGN PATENT DOCUMENTS

| | | |
|---|---|---|
| DE | 19513293 | 10/1996 |
| EP | 1510228 | 3/2005 |
| GB | 2122903 | 1/1984 |

OTHER PUBLICATIONS

International Search Report (with English translation) for corresponding International Application No. PCT/EP2010/006748 mailed Mar. 4, 2011.

* cited by examiner

*Primary Examiner* — Sean E Conley
(74) *Attorney, Agent, or Firm* — Myers Wolin, LLC

(57) ABSTRACT

A method and device for producing a fragranced air stream for fragrancing rooms, objects or the like, wherein fragrance is applied to a strip-like fragrance carrier (4) which is moved in an evaporation duct (1) through which fresh air flows. The fragrance is applied onto the moving fragrance carrier (4) by means of specific spraying before the fragrance carrier (4) enters the evaporation duct (1), and the fragrance carrier (4) is discarded as waste after exiting the evaporation duct (1).

8 Claims, 2 Drawing Sheets

METHOD AND DEVICE FOR PRODUCING A FRAGRANCED AIR STREAM

CROSS REFERENCE TO RELATED APPLICATIONS

The present application is a continuation of International Application No. PCT/EP2010/006748 filed Nov. 5, 2010, which claims priority to German Patent Application No. 10 2009 052 267.0 filed on Nov. 6, 2009, the contents of each of which are incorporated herein by reference.

FIELD OF THE INVENTION

The invention relates to a method and a device for producing a fragranced air stream for fragrancing rooms, objects or the like.

BACKGROUND

A known method for producing a fragranced air stream is described in U.S. Pat. No. 2,410,488. In that case a strip-like fragrance carrier is moved forward and back in the interior of an evaporation shaft, while a stream of fresh air flows through the evaporation shaft.

In known fragrancing devices, the fragrance is admixed by exposing fragrance gel or fragrance granules in a stream of fresh air. The fragranced fresh-air stream is then either passed directly into a room to be fragranced or supplied to an air-supply or air-conditioning system, so that the fragrance can be dispersed into the rooms connected thereto.

The use of such fragrancing devices usually leads very rapidly to reduction of the quality of the produced fragranced-air stream by demixing at surfaces and oxidation. Particular difficulties are already encountered in changing the fragrance, since this is successful only when the entire equipment has been thoroughly cleaned to eliminate all residues of the previously used fragrance.

For better understanding of the relationships and causes, it will be assumed that the fragrances used for fragrancing of rooms are most usually complex mixtures of ethereal oils, such as orange oil, peppermint oil, etc. and individual fragrances. The latter are optionally fragrances that are natural, identical to natural, semisynthetic or completely synthetic, for example from geraniol, menthol, Cedramber, galaxolide, etc.

In total, approximately 3000 fragrance components are available to the perfumer as the person skilled in the art of fragrance mixtures. These are characterized by different evaporation temperatures and rates, fragrance intensities, oxidation resistances, duration of action, etc.

Despite relatively short maintenance intervals, surfaces coming into contact with the fragrance, especially in the vicinity of the dosing device or of flow ducts, lead to disadvantageous coatings, for example due to resinification of fragrance residues or due to sooting with liquid residual components of the arriving fragranced air. In many cases the fresh aromas are already masked or demixed after a few hours, and instead fragrance residues creating a stale and depleted impression escape. Maintenance intervals that are too long very rapidly lead to contamination of entire ventilation systems, often caused by use of sprays as dosing devices. On the other hand, no improvement is achieved even by overdosing the fragrance concentrations introduced into a ventilation system. To the contrary, the consequence is overstimulation of the sensory perception in people who spend time in the fragranced room, frequently accompanied by headaches.

It is self-evident that spontaneous changes of fragrance are ineffective in contaminated ventilation systems, since the deposited fragrance droplets are still released to the arriving fresh air hours or even days later, with the unpleasant consequence that indefinable fragrance mixtures are formed after a change of fragrance.

SUMMARY

In contrast, the object underlying the present invention is to improve the technology of air fragrancing and of changing fragrances to the effect that rapid demixing and oxidation of the fragrances is prevented, that deposition of fragrances on the equipment side is largely suppressed and that rapid changes of fragrance are possible without associated impairment of effect, wherein the maintenance intervals for the equipment are significantly prolonged. Moreover, the inventive technology is intended to permit extensive automation in the production and dispersion of the fragranced air stream as well as exact dosing thereof according to specified fragrance intensity.

In this connection, it is of particular importance, both for application of the fragrance on the fragrance carrier and for passage thereof through the evaporation shaft, that the fragrance is applied on the advancing strip-like fragrance carrier without wetting the environment, for example in a dosing device, advantageously by purposeful spraying onto the fragrance carrier before it enters the evaporation shaft, and that furthermore the wetted fragrance carrier does not come into direct contact with any part of the wall of the evaporation shaft while it is in the evaporation shaft. In this way it is assured that the fresh air streaming past the fragrance carrier in the evaporation shaft picks up the fragrance exclusively in gaseous form, or in other words in the form of the molecules of the fragrance mixture escaping by evaporation from the fragrance applied as liquid. In this way, any transport of liquid fragrance droplets in the fragranced air stream is suppressed, as is therefore the danger of contamination of the equipment side.

To favor evaporation in the evaporation shaft, heated fresh air is advantageously passed therethrough. The temperature thereof should then be well above room temperature, to ensure that all fragrance components are able to evaporate during transport of the fragrance in the evaporation shaft. In this way it is intended that the evaporation will be accelerated, although the shortest possible heating should be achieved in order to maintain the quality of the fragrances.

In this regard it will be expedient to ensure that the fragrance carrier is drawn through the evaporation shaft with adjustable speed. In this way it is possible, in association with the temperature of the heated fresh air, to achieve an optimum evaporation result with controlled concentration and constant quality of the fragrance in the fragranced air stream.

By further configuring the inventive method such that the amount of fragrance applied on the fragrance carrier per unit length can be finely regulated to determine the fragrance concentration, another objective is to achieve fragrancing largely automatically, as can be achieved, for example, by means of appropriate computer programs. These permit not only control of the fragrancing duration or achievement of a desired fragrance intensity, but also changing of the fragrance by spontaneous selection of different fragrances, which are stored in a plurality of alternatively connectable fragrance containers.

These fragrance containers are advantageously stored under cool conditions, for example within a temperature range of 10-15° C. To introduce the fragrance from the container, the content thereof is expediently under the pressure of an inert gas such as nitrogen (N2) or argon (Ar), whereby harmful oxidation of the fragrance by atmospheric oxygen is prevented.

An inventive device suitable for performing the inventive method is characterized in that an evaporation shaft through which fresh air flows is provided, in that the evaporation shaft has an inlet aperture for a strip-like fragrance carrier wetted with fragrance and an outlet aperture for extracting this from the evaporation shaft after release of fragrance into the fresh air stream, and in that the dosing device is connected upstream and an extraction device for the fragrance carrier is connected downstream from the evaporation shaft.

The fragrance carrier is therefore pulled by means of the extraction device through the evaporation shaft in such a way that it transits this while heated fresh air flows through the evaporation shaft and thus becomes enriched with the fragrance entrained by the fragrance carrier.

According to an advantageous configuration in this regard, it is provided that the fragrance carrier is pulled out of a supply drum and successively through the dosing device and the evaporation shaft and is ultimately pulled into a waste drum.

For this purpose the extraction device preferably comprises interacting rotating members, between which the fragrance carrier is conveyed by traction. Advantageously toothed gears meshing with one another are possible as rotating members, acting in such a way that the fragrance carrier can be pulled without slipping through the evaporation shaft. For introduction of the consumed end of the fragrance carrier into the waste drum, there is expediently provided a further traction device inside the waste drum, for example in the form of a winding roll driven in rotation. According to the invention, the dosing device is configured in such a way that the fragrance can be sprayed in liquid form without losses onto the moving fragrance carrier. For this purpose the dosing device comprises nozzles for purposeful spraying of the finest amounts of fragrance onto the moving fragrance carrier, which is formed, for example, as a wick-like thread, as a tape, as a narrow fabric web or possibly as an absorptive film, each of which can be pulled from the supply drum by an appropriate supply roll. In this connection it is self-evident that the fragrance is received in droplet form on the surface or in the interior of the material of the fragrance carrier, in order to separate therefrom in gaseous form during passage through the evaporation shaft, wherein the fragrance molecules are entrained by the heated fresh air flowing through the evaporation shaft.

It is particularly desirable for the fragrance to be applied on the fragrance carrier as free of residues as possible; liquid transport techniques such as are employed analogously in inkjet printers are suitable for this purpose.

The fragranced air stream emerging from the evaporation shaft is then mixed with the supply air in a ventilation or air-conditioning system or, for example, is supplied through a perforated plate to a room connected thereto. During the entire transport path of the fragrance, first on the fragrance carrier and then in the fragranced air or supply air, deposition of fragrance as droplets is prevented, and so contamination within the inventive fragrancing device is reliably suppressed. Thus special cleaning measures are also obviated, especially also in connection with a change of fragrance. This merely requires that the dosing device be changed over to a new fragrance, which advantageously takes place only after the fragrance carrier, if still wetted with the previous fragrance, has completely passed through the evaporation shaft.

Within the scope of the invention, it is expedient that the dosing device and extraction device be electronically regulable for control of the dosing concentration, and also that, in the case of a plurality of fragrances, the change of fragrance is programmable by means of an electronic controller. One prerequisite for this is that a plurality of fragrance containers with different fragrances can be activated sequentially.

By means of an appropriate computer program, the capability then exists of controlling the inventive device completely automatically, for example with changes of fragrances corresponding to a predetermined photo sequence or the progress of a film, such as film sequences for advertising purposes. Adapted in this way the capability exists of offering changes of fragrances, for example in the supply air of a ventilation system, or in other words of delivering different fragrance varieties with controllable fragrance concentration, distinguishable according to flowers, fruits, woods, spices, etc. For example, if consumers can no longer notice a stimulating citrus fragrance because of accustomization over a lengthy period, this may be alleviated by varying supply of comforting fragrances, for example characterized according to herbs, lime blossoms, verbena or other aromas, such as orange or grapefruit.

Within the scope of the invention, not only fragrancing of rooms but also fragrancing of other objects with cavities may be achieved, examples being furniture—tables, chairs, cabinets, beds, commodes.

Furthermore, the fragranced fresh air may also be supplied directly, or in other words without being detoured through an air-conditioning system, to an open or closed space to be fragranced, such as a stadium or an urban landscape. Finally, instead of an evaporation shaft closed transversely relative to the flow direction, another alternative is an evaporation shaft open transversely relative to the flow direction on one side, for example in the manner of a floor duct, orchestra pit or even a natural valley with a wind flow.

Advantageously fresh air is used as the flowing medium for the fragrance admixed in the evaporation shaft; however, other gaseous flowing media are also suitable, for example in the form of elemental gases such as nitrogen or other inert gases.

BRIEF DESCRIPTION OF THE DRAWINGS

An embodiment of the invention will be explained hereinafter on the basis of the drawings, wherein.

DETAILED DESCRIPTION

At the center of the fragrancing device there is disposed an evaporation shaft 1, which is connected with its lower end to a fresh-air duct 2. The fresh air flowing in according to arrow F passes through a heater 3, which surrounds a portion of fresh-air duct 2 and heats the fresh air flowing therein well above room temperature. To favor evaporation in evaporation shaft 1, the temperature of the fresh air entering evaporation shaft 1 lies between 40 and 80° C., although even higher temperatures are also adjusted in exceptions.

Figure 2:
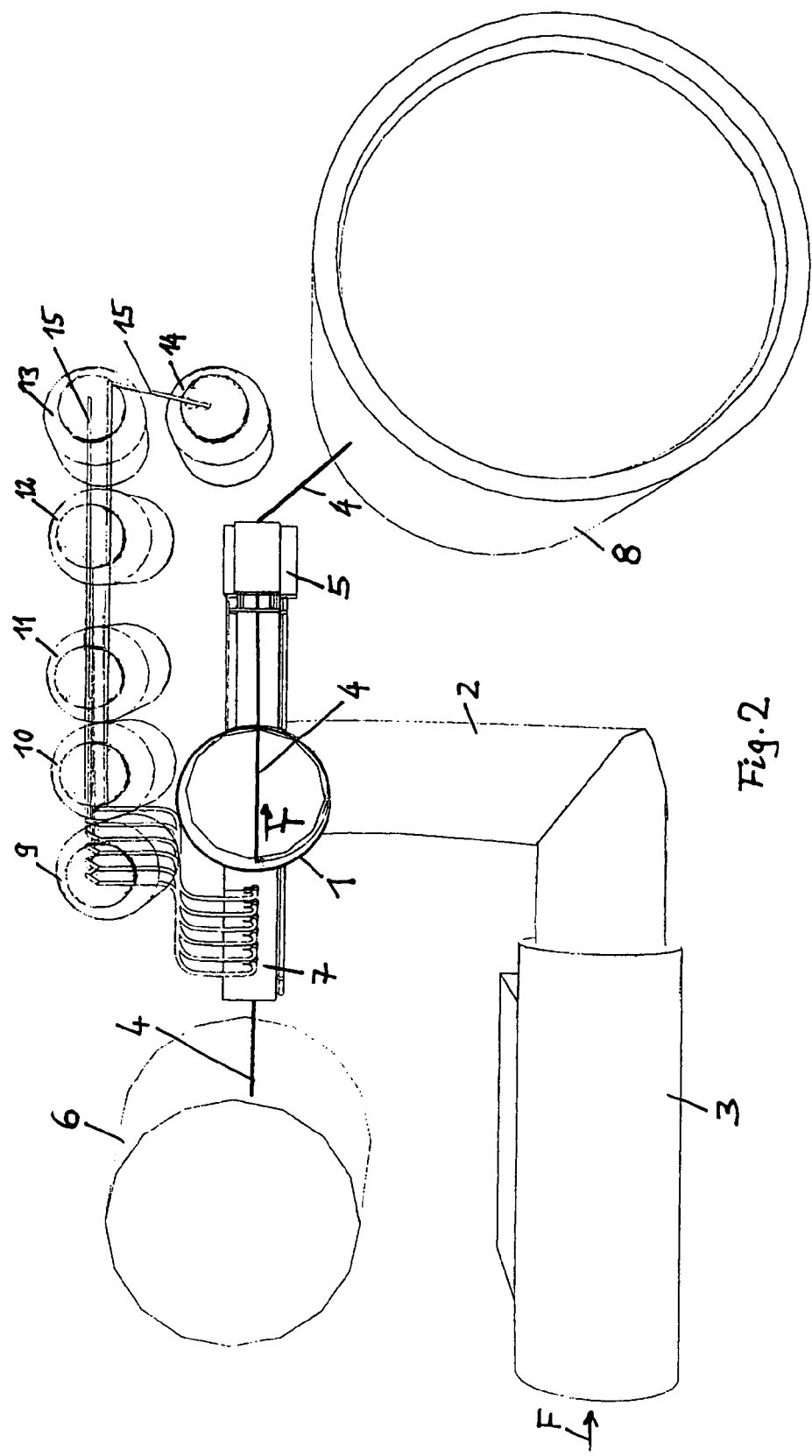
FIG. 2 shows the fragrancing device according to FIG. 1 in top view.

A wick-like thread 4 is used as fragrance carrier. As illustrated in FIG. 2, it transits evaporation shaft 1 in the direction of arrow T. As yet unwetted fragrance carrier 4 is pulled out of a supply drum 6 by means of an extraction device 5 downstream from evaporation shaft 1, passes through a dosing device 7, then transits evaporation shaft 1 and downstream from extraction device 5 is passed by means of a traction device, not illustrated, into the interior of a waste drum 8.

Connected to dosing device 7 are in total six fragrance containers 9 to 14 for different fragrances, which are in communication via respective pressure lines 15 with nozzles, not illustrated in more detail, within dosing device 7.

Figure 1:
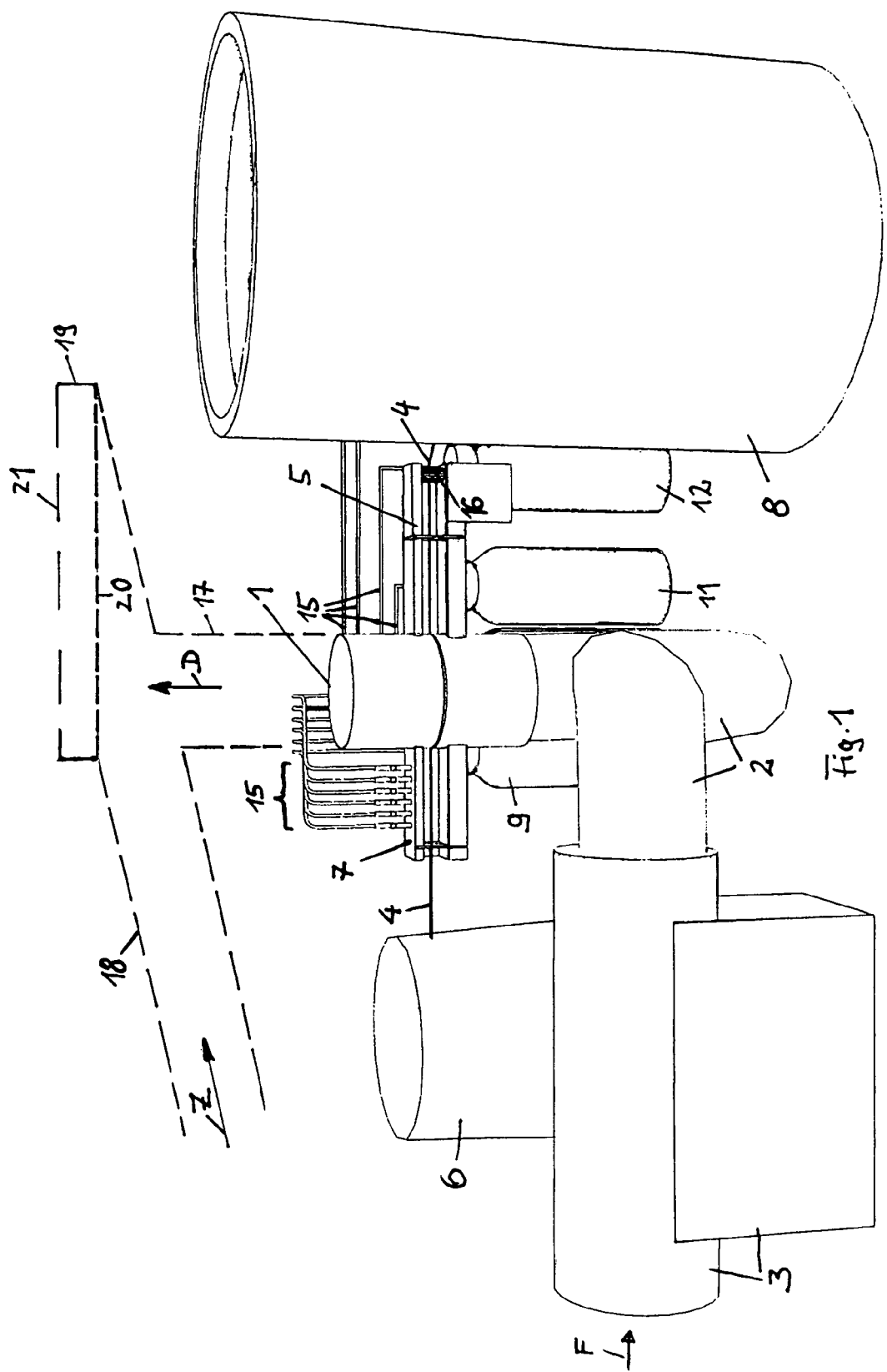
FIG. 1 shows a fragrancing device in side view.

FIG. 1 shows fragrance carrier 4 on the path of its thread through dosing device 7 to the entry into evaporation shaft 1 and after its exit from evaporation shaft 1 further through extraction device 5 and from there further into waste drum 8. To assure slip-free transport of strip-like fragrance carrier 4, a toothed gear 16 of a toothed-gear pair, which serves for uniform transport of the fragrance carrier in the direction of arrow T, is shown in the interior of extraction device 5.

For simplicity, no control devices of any kind are shown in the drawing. Nevertheless, the fragranced air emerging according to arrow D from evaporation shaft 1 through a secondary air duct 17 is evident by virtue of the dashed lines. The fragranced air flows into a supply-air duct 18 of an air-supply and air-conditioning system, where the air-conditioned supply air flowing in according to arrow Z becomes mixed with the fragranced air from secondary air duct 17. Supply-air duct 18 is connected to a screen 19, via which the fragranced supply air reaches the room located thereabove. Screen 19 comprises two perforated plates, namely a lower perforated plate 20 with relatively small holes and an upper perforated plate 21, disposed thereabove, with somewhat larger outlet holes, through which the fragranced air flows into the room. Lower perforated plate 20 with the smaller hole array causes a slight backdraft of the supply air, thus ensuring that a uniform flow distribution can be achieved. This arrangement permits particularly quick changes of fragrance. The fragranced air stream can also be connected very simply as a bypass to an existing air-conditioning system.

By the fact that strip-like fragrance carrier 4 is conveyed practically without contact between supply drum 6 and waste drum 8, it is possible to operate the fragrancing device without contaminating it by fragrance droplets. Only in this way are problem-free changes of fragrance achieved, while any desired number of fragrance containers can be connected.

In this respect it is important that the nozzles at the end of pressure lines 15 are formed in such a way within dosing device 7 that fragrance droplets can emerge purposefully therefrom and land accurately on the moving fragrance carrier. Strip-like fragrance carrier 4 will therefore be dimensioned in such a way and its absorptiveness will be selected in such a way that it is capable of absorbing the liquid fragrance completely without backspatter, while at the same time being capable of permitting evaporation of the fragrance and transfer thereof in gaseous form into the heated fresh-air stream during transit through evaporation shaft 1. The spent end of fragrance carrier 4 wound up in the waste container is disposed of as waste at specified intervals. At all times, only clean carrier material, which is scheduled only for single use, is pulled out of supply drum 6.

We claim:

1. A device for producing a fragranced air stream for fragrancing rooms or other objects, comprising:
    a dosing device (7) for admixing one or more fragrances from separate fragrance containers (9-14), and an evaporation shaft (1) through which fresh air flows;
    wherein the evaporation shaft (1) has an inlet aperture for an elongated fragrance carrier (4) wetted with fragrance and an outlet aperture for extracting the fragrance carrier from the evaporation shaft (1) after release of fragrance into the fresh air stream,
    wherein the dosing device (7) is connected upstream and an extraction device (5) for the fragrance carrier (4) is connected downstream from the evaporation shaft (1);
    wherein the dosing device (7) comprises nozzles for purposeful spraying of fragrance onto the moving fragrance carrier (4) in such a way that the fragrance can be sprayed in liquid form without losses onto the moving fragrance carrier; and
    wherein the fragrance carrier (4) is pulled by means of the extraction device (5) out of a supply drum (6) and pulled successively through the dosing device (7) and the evaporation shaft (1) and is ultimately pulled into a waste drum (8), whereby the consumed end of the fragrance carrier (4) is introduced into the waste drum (8) by a further traction device inside the waste drum (8).

2. A device according to claim 1, characterized in that the extraction device (5) comprises interacting rotating members, between which the fragrance carrier (4) is conveyed by traction.

3. A device according to claim 2, characterized in that the rotating members are toothed gears (16) meshing with one another in such a way that the fragrance carrier (4) can be pulled without slipping through the evaporation shaft (1).

4. A device according to claim 1, characterized in that the fragranced air stream is mixed with the supply air of a ventilation or air-conditioning system.

5. A device according to claim 1, characterized in that the fragranced air stream is passed through a perforated plate (19) into a room.

6. A device according to claim 1, characterized in that the dosing device (7) and extraction device (5) are electronically regulable for control of the dosing concentration.

7. A device according to claim 1, characterized in that, in the case of a plurality of fragrances, the change of fragrance is programmable by means of an electronic controller.

8. A device according to claim 1, characterized in that a plurality of fragrance containers (9-14) with different fragrances can be activated sequentially.

* * * * *